United States Patent [19]

Lappe et al.

[11] Patent Number: 5,294,415

[45] Date of Patent: Mar. 15, 1994

[54] PROCESS FOR THE SEPARATION AND RECOVERY OF RHODIUM FROM THE PRODUCTS OF THE OXO SYNTHESIS

[75] Inventors: Peter Lappe, Dinslaken; Ludger Bexten, Hünxe; Dieter Kupies, Duisburg, all of Fed. Rep. of Germany

[73] Assignee: Hoechst Aktiengesellschaft, Fed. Rep. of Germany

[21] Appl. No.: 903,010

[22] Filed: Jun. 23, 1992

Related U.S. Application Data

[63] Continuation of Ser. No. 676,891, Mar. 28, 1991, abandoned, which is a continuation of Ser. No. 372,050, Jun. 27, 1989, abandoned.

[30] Foreign Application Priority Data

Jun. 30, 1988 [DE] Fed. Rep. of Germany ....... 3822037

[51] Int. Cl.$^5$ ...................... C01G 55/00; C22B 11/00; B01J 38/48; B01J 38/64
[52] U.S. Cl. ........................................ 423/22; 502/22; 502/25; 502/29; 502/30; 502/31; 502/32; 502/34
[58] Field of Search ...................... 423/22; 502/22, 24, 502/25, 29-34, 38, 55, 56; 556/21; 568/451, 454

[56] References Cited

U.S. PATENT DOCUMENTS

| | | | |
|---|---|---|---|
| 4,021,463 | 5/1977 | Kummer et al. | 502/27 |
| 4,990,639 | 2/1991 | Bexten et al. | 423/22 |
| 5,091,350 | 2/1992 | Cornils et al. | 502/24 |

FOREIGN PATENT DOCUMENTS

| | | | |
|---|---|---|---|
| 0147824 | 7/1985 | European Pat. Off. | 423/22 |
| 3626536 | 2/1988 | Fed. Rep. of Germany | 423/22 |

Primary Examiner—Wayne Langel
Assistant Examiner—Steven Bos
Attorney, Agent, or Firm—Bierman and Muserlian

[57] ABSTRACT

To separate and recover rhodium, the distillation residues of oxo synthesis products are initially treated with an oxidant. Then the reaction mixture is reacted, in the presence of carbon monoxide (or a compound which splits off carbon monoxide), with an aqueous solution of a reagent forming a water-soluble complex compound with rhodium. The reaction mixture breaks into an organic phase and an aqueous phase, the complex goes to the aqueous phase as it is substantially insoluble in the organic phase.

28 Claims, No Drawings

PROCESS FOR THE SEPARATION AND RECOVERY OF RHODIUM FROM THE PRODUCTS OF THE OXO SYNTHESIS

PRIOR APPLICATION

This application is a continuation of U.S. patent application Ser. No. 676,891 filed Mar. 28, 1991, now abandoned, which is a continuation of U.S. patent application Ser. No. 372,050 filed Jun. 27, 1989, now abandoned.

This Application claims the priority of German Application P 38 22 037.7, filed Jun. 30, 1988.

The present invention relates to an improved process for separating and recovering rhodium from the reaction mixtures of the oxo synthesis.

BACKGROUND OF THE INVENTION

The preparation of aldehydes and alcohols by the addition of carbon monoxide and hydrogen to olefinic double bonds (hydroformylation) is known. The reaction is catalyzed by metals of the 8th subgroup of the Periodic Table or their compounds which form carbonyls or hydridocarbonyls under the reaction conditions. While formerly cobalt and cobalt compounds were used almost exclusively as catalysts, rhodium catalysts are increasingly favored today even though rhodium is many times more expensive than cobalt. Rhodium is used alone or in combination with complexing agents, e.g. organic phosphines. While the oxo synthesis requires reaction pressures of 25 to 30 MPa with rhodium as a catalyst, pressures of 1 to 5 MPa are sufficient if rhodium complex compounds are used.

There are clear advantages to the use of rhodium catalysts in many cases. They have higher activity and selectivity, and also permit uncomplicated operation of the production facility, in particular with regard to the performance of the synthesis and the removal of the products from the reactor. Finally, the classic oxo process based on cobalt catalysts can be converted to rhodium catalysts using the existing apparatus, in many cases with little additional capital expenditure.

However, the loss-free or at least nearly loss-free separation and recovery of rhodium causes considerable problems, regardless of whether it is used as a catalyst with or without an additional complexing agent. After completion of the reaction, the rhodium is to be found dissolved in the hydroformylation product as a carbonyl compound which can also contain further ligands.

For work-up, the oxo raw product is normally pressure-relieved in several stages by reducing the synthesis pressure (which is approximately 1 to 30 MPa depending on the type of rhodium catalyst used) initially to about 0.5 to 2.5 MPa and the synthesis gas dissolved in the raw product is then released. Thereafter, the pressure can be reduced to normal. The rhodium is separated either directly out of the raw product or out of the residue of the raw product distillation. The first route is taken when rhodium has been used as a catalyst in the previous hydroformylation stage without an additional complexing agent.

The second variation is used when the rhodium catalyst contains not only carbon monoxide but also other ligands, e.g. phosphines or phosphites in complex bonding. The latter can also be used when hydroformylation is carried out with rhodium alone but a complexing agent is added to the raw product to stabilize the rhodium after the pressure has been relieved. It must always be remembered that the noble metal is only present in the raw product in a concentration of a few ppm, therefore it must be separated very carefully. Additional difficulties can be caused by the rhodium partly changing into metallic form or forming polynuclear carbonyls during pressure relief, especially when it is used without a ligand. Then a heterogeneous system is formed which consists of the liquid organic phase and the solid phase containing rhodium or rhodium compounds.

Several processes for separating rhodium from the oxo raw product are known. According to the procedure described in DE 33 47 406 A1, rhodium is recovered from the oxo raw product by extraction with complexing reagents. According to a preferred embodiment, sulfonates and carboxylates of organic phosphines are used as complexing agents.

Sulfonated triphenylphosphines, e.g. salts of triphenylphosphine trisulfonic acid, are particularly suitable complexing reagents. The complex compounds formed from rhodium and the sulfonates or carboxylates of the organic phosphines are water-soluble. Thus, the rhodium can be extracted from the oxo raw product, i.e. the organic phase, with an aqueous solution of the substituted phosphine. The aqueous, rhodium-containing phase can be separated from the organic product mixture by simple decantation. High rhodium concentrations can be achieved in the solution of the complexing agent by recirculation.

In order to accelerate and complete extraction of the rhodium from the organic phase and its transfer to the aqueous phase, a solubilizer is added to the aqueous solution of the complexing agent according to DE 34 11 034 A1. This is particularly effective because it changes the physical properties of the interface between the two liquid phases. Thus, the introduction of the aqueous extracting agent into the product phase and the transfer of the rhodium from the product phase into the aqueous complexing agent phase is accelerated, extraction is simplified, and the apparatus required is reduced.

The higher the concentration of the solubilizer in the aqueous phase, the more rhodium is extracted. However, the amount of solubilizer cannot be increased infinitely because it affects the aqueous solution of the extracting agent and impairs its stability. Therefore, the process described in DE 34 43 474 A1 uses quaternary ammonium salts of sulfonated triphenylphosphines as complexing agents. However, it is very costly to produce these salts, which makes the extraction process not always economically feasible.

Various processes are also known for separating the rhodium from the distillation residues of the oxo raw product. According to the process in EP 15 379 A1, the rhodium-ligand catalysts used in the oxo synthesis are oxidized, e.g. with air in the presence of aldehyde, and the solid reaction products thus formed are removed. The solution obtained can be reused as a catalyst after the liquid has been replenished. This procedure has its limitations because the residues formed during distillation are not separated.

The subject of U.S. Pat. No. 4,400,547 is a hydroformylation process in the presence of unmodified rhodium as a catalyst. After a phosphorus ligand such as triphenylphosphine has been added to the oxo raw product, the aldehyde is distilled off. Then the distillation residue is treated with oxygen to split off the ligand from the complex compound again and to recover the rhodium in its active form. Therefore, complete separation of the rhodium and distillation residue is not possible with this procedure.

Separation of noble metals such as rhodium from high-boiling hydroformylation residues is described in US-PS 3 547 964. In this process the residues are treated with hydrogen peroxide in the presence of acids such as formic acid, nitric acid or sulfuric acid. Owing to the high price of hydrogen peroxide and the problems in handling it, the commercial applications of this process are limited.

According to DE 24 48 005 C2, a distillation residue containing rhodium is initially treated with acids and peroxides. Then excess peroxides are destroyed by heating and the aqueous solution containing the catalyst metal is reacted, in the presence of a water-soluble organic solvent, with hydrohalic acid or alkali halides, as well as with tertiary phosphines and carbon monoxide or compounds which split off carbon monoxide. This procedure again requires the use of peroxides accompanied by the above-mentioned economic disadvantages and the use of halogen-resistant materials.

Therefore, the problem was to a process which permits the recovery of rhodium from residues obtained during the distillation of reaction mixtures from the oxo synthesis as simply and completely as possible.

DESCRIPTION OF THE INVENTION

According to the invention, this problem is solved by a process wherein the distillation residues are first reacted with an oxidant and then, in the presence of carbon monoxide or a compound splitting off carbon monoxide, with an aqueous solution of a reagent forming a water-soluble complex compound with rhodium.

The term distillation residues is understood to be the high-boiling parts of the hydroformylation products which remain after both the first runnings containing inter alia hydrocarbon and the aldehydes and alcohols have been distilled off. The residues consist mainly of products arising from the condensation of aldehydes with each other and the reaction of aldehydes with alcohols. They also contain catalytic rhodium and, as ligands, compounds which react with the rhodium to form complexes. Such ligands are, for example, organic phosphines such as triphenylphosphine. They are present in the hydroformylation mixture from the very beginning and are a component of the catalyst, or they are added to the reaction mixture after completion of the hydroformylation reaction but before distillation. Their purpose is to stabilize the rhodium compounds against thermal loading in order to prevent precipitation of insoluble rhodium compounds or metallic rhodium.

According to the invention, the distillation residues are treated with an oxidant; oxygen or oxygen-containing gases, preferably air, are particularly suitable. However, other oxidants can also be used. Examples of oxidants which have proved valuable are hydrogen peroxide and compounds forming hydrogen peroxide such as sodium peroxide and also hypochlorites and permanganates. Oxidation takes place at 20° to 200° C., in particular 50° to 150° C. and preferably 80° to 120° C. It is not necessary to apply pressure but it is often advantageous in order to reduce the reaction time. Pressures of 0.1 to 5 MPa have proved valuable. It is also recommended that the oxidizing gases be distributed as finely as possible in the distillation residue by means of suitable apparatus. The reaction time depends on the conditions selected. With discontinuous operation it is 0.1 to 10 hours, preferably 2 to 5 hours.

Following the oxidation, the distillation residues are treated with an aqueous solution of a compound which forms a complex with rhodium. According to the invention, the compounds selected as complexing agents are those which, under the temperature conditions used, enter into stabler complexes with rhodium than rhodium does with carbon monoxide. The more the complexing reagents have a tendency to react with rhodium, the more complete the rhodium separation is. Moreover, the complex compound must be soluble in water but not in organic media.

The complexing agents preferred for rhodium are phosphorus compounds which contain phosphorus atoms capable of forming coordination bonds with the noble metal, i.e. phosphorus atoms with free electron pairs. Of these compounds, the sulfonates and carboxylates of organic phosphines are particularly suitable. These compounds have the general formula:

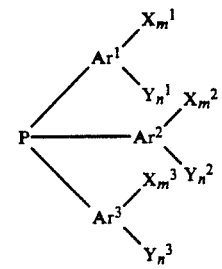

where $Ar^1$, $Ar^2$, $Ar^3$ are each a phenyl or naphthyl group; $Y^1$, $Y^2$, $Y^3$ each denote a straight or branched chain alkyl group with 1 to 4 carbon atoms, a straight or branched chain alkoxy group with 1 to 4 carbon atoms, a halogen atom, or an OH, CN, $NO_2$, or $R^1R^2N$ group in which $R^1$ and $R^2$ each stand for a straight or branched chain alkyl group with 1 to 4 carbon atoms; $X^1$ $X^2$ and $X^3$ are each a carboxylate (COO—) or a sulfonate ($SO_3$—) group; $m_1$, $m_2$, $m_3$ are individually integers from 0 to 3, at least one of $m_1$, $m_2$ or $m_3$ being equal to or greater than 1; and $n_1$, $n_2$, $n_3$ are individually integers from 0 to 5. The cations which the above-mentioned carboxylates and sulfonates contain are alkali metal, alkaline earth metal, zinc, ammonium or quaternary ammonium ions of the general formula $N(R^3R^4R^5R^6)+$ in which $R^3$, $R^4$, $R^5$, $R^6$ each stand for a straight or branched chain alkyl group with 1 to 4 carbon atoms.

According to a preferred embodiment of the claimed process, compounds of the aforementioned general formula are used as complexing reagents where $Ar^1$, $Ar^2$, $Ar^3$ each denote a phenyl group, $X^1$, $X^2$, $X^3$ each stand for a sulfonate group, and $m_1$, $m_2$, $m_3$ each denote the number 0 or 1, the sum of $m_1$, $m_1$ and $m_3$ being 1, 2 or 3.

According to the invention, the oxidized distillation residue is treated with the complexing agent in the presence of carbon monoxide or a compound splitting off carbon monoxide. At least 100 moles, preferably 300 to 1000 moles of carbon monoxide (or the equivalent amount of a compound splitting off carbon monoxide), are added per g-atom of rhodium in the distillation residue. The reaction takes place at temperatures of 50° to 160° C., in particular 90° to 130° C. and normally at pressures of 10 to 40 MPa, preferably 20 to 30 MPa. The treatment time, i.e. the time taken to extract the rhodium from the organic phase with the aid of the aqueous solution of the complexing agent, is 0.1 to 10 hours, in particular 0.5 to 2 hours.

Carbon monoxide can be used in pure form but also as a mixture in synthesis gas.

Formaldehyde, preferably as an aqueous solution, is particularly suitable as a compound forming carbon monoxide under the reaction conditions. The use of aqueous formaldehyde solution has the advantage that no pressure is required.

After the reaction has been completed, the mixture is left to cool and the organic and aqueous phases are separated from each other. The phase separation can be improved by adding an inert solvent, e.g. a hydrocarbon such as toluene or xylene, to the reaction mixture. Any remaining amounts of rhodium can be recovered from the separated organic phase by washing with water.

The claimed process is particularly successful when used to separate and recover rhodium from the distillation residues of the hydroformylation of ethylene and terminally and internally branched olefins such as i-heptene, diisobutylene, tripropylene, tetrapropylene, and/or the mixture of $C_8$ olefins marketed under the name Dimersol. Naturally, the process can also be applied to the hydroformylation of unbranched terminal and central olefins where the absolute rhodium concentrations are generally lower.

The aqueous phase containing high concentrations of rhodium can either be used again as a catalyst solution directly or first cleaned and concentrated. It is also possible to separate out the rhodium as a compound which is only slightly soluble or insoluble in water, e.g. as rhodium-2-ethylhexanoate, and to then put it to further use.

In the following examples the invention is explained. Naturally, it is not intended to restrict it to these special embodiments. The abbreviations TPPTS and TPPDS stand for triphenylphosphine trisulfonate and triphenylphosphine disulfonate.

EXAMPLE 1

200 g of a distillation residue from the hydroformylation of i-heptene containing 328 ppm of rhodium are placed in a 1-liter glass autoclave. At an internal temperature of 27° to 30° C., the pressure is adjusted to approximately 0.4 MPa while stirring. Then the residue is heated to 100° C. over a period of about 30 minutes, 120 liters of air being passed through the autoclave contents during this time. Another 190 liters of air are passed through the reaction solution over a period of 60 minutes at a temperature of 100° C. Then the reactor contents are cooled to room temperature and mixed with 50 g of an aqueous TPPTS solution containing 23.7% by weight of TPPTS and 4.88% by weight of TPPDS and with 50 g of 37% formalin. The reaction mixture is then stirred at 116° to 122° C. for 1 hour.

After cooling to 80° C., 50 g of toluene are added and the autoclave contents stirred for 5 minutes. The phases are separated and the organic phase extracted again with 50 g of water. The organic phase (257 g) still contains 9 ppm of rhodium, corresponding to a rhodium separation of 96.5%.

EXAMPLE 2

As described in Example 1, 200 g of a distillation residue from the hydroformylation of i-heptene are treated with air. Then 50 g of TPPTS solution (23.7% by weight of TPPTS and 4.88% by weight of TPPDS) are added and the reaction mixture stirred for 1 hour at a temperature of 120° C. and a synthesis gas pressure of 25 MPa. After cooling, addition of 180 g of toluene, and phase separation, the remaining organic phase is washed twice, each time with 50 g of water. The organic phase (379 g) still contains 3 ppm of rhodium, corresponding to a rhodium separation of 98.3%.

EXAMPLE 3

The same procedure is adopted as in Example 1, the only difference being that no formalin is added. The organic residue (249 g) still contains 23.7 ppm of rhodium corresponding to a rhodium separation of 91%.

EXAMPLE 4

The same procedure is adopted as in Example 1, the only difference being that a distillation residue from the hydroformylation of i-octene containing 148 ppm of rhodium is used. The organic residue (258 g) still contains 4.9 ppm of rhodium corresponding to a rhodium separation of 95.7%.

EXAMPLE 5

The same procedure is adopted as in Example 2, the only difference being that a distillation residue from the hydroformylation of i-octene containing 148 ppm of rhodium is used. The organic residue (377 g) still contains 0.8 ppm of rhodium corresponding to a rhodium separation of 99%.

EXAMPLE 6

The same procedure is adopted as in Example 3, the only difference being that a distillation residue from the hydroformylation of i-octene containing 148 ppm of rhodium is used. The organic residue (247 g) contains 11 ppm of rhodium corresponding to a rhodium separation of 90.8%.

What we claim is:

1. A process for the recovery of a rhodium or a rhodium-containing catalyst from a distillation residue of a mixture of oxo synthesis products consisting essentially of reacting the distillation residue with an oxidizing agent to form a mixture, reacting the mixture in the presence of carbon monoxide or a carbon monoxide forming compound with an aqueous solution of a reagent which forms a more stable water soluble but organic media insoluble complex with rhodium than a complex with carbon monoxide, said reagent having the formula

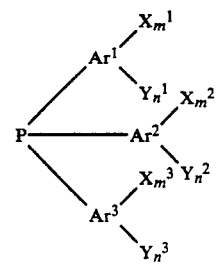

wherein $Ar^1$, $Ar^2$ and $Ar^3$ are each a phenyl or naphthyl group; $Y^1, Y^2, Y^3$ each denote a straight or branched chain alkyl group with 1 to 4 carbon atoms, a straight or branched chain alkoxy group with 1 to 4 carbon atoms, a halogen atom, or an OH, —CN, —NO$_2$, or R$^1$R$^2$N— group in which $R^1$ and $R^2$ each stand for a straight or branched chain alkyl group with 1 to 4 carbon atoms, $X^1$, $X^2$ and $X^3$ are each a carboxylate (COO—) or a sulfonate (SO$_3$—) group; $m_1$, $m_2$, $m_3$ are individually integers from 0 to 3, at least one $m_1$, $m_2$ or $m_3$ being equal to or greater than 1; and $n_1$, $n_2$, $n_3$ are individually integers from 0 to 5, treating the mixture with an inert organic solvent, recovering the aqueous phase containing the water soluble complex of rhodium and reusing the same as a hydroformylation catalyst.

2. The process of claim 1 wherein said distillation residue contains ligands which react with rhodium to form complexes.

3. The process of claim 2 wherein said ligands are organic phosphines.

4. The process of claim 2 wherein said ligands are added after completion of said oxo synthesis and before distillation thereof.

5. The process of claim 1 wherein said oxidizing agent is oxygen, oxygen-containing gas, hydrogen peroxide, sodium peroxide, hydrochlorides, permanganates, and mixtures thereof.

6. The process of claim 5 wherein said oxidizing agent is air.

7. The process of claim 1 wherein the reaction with the oxidizing agent is carried out at an oxidation temperature of 20° to 200° C.

8. The process of claim 1 wherein the reaction with the oxidizing agent is carried out at an oxidation pressure of 0.1 to 5 MPa.

9. The process of claim 1 wherein said oxidizing agent is finely distributed in the distillation residue.

10. The process of claim 1 wherein is the reaction with the oxidizing agent carried for a time of 0.1 to 10 hours.

11. The process of claim 10 wherein said time is 2 to 5 hours.

12. The process of claim 1 wherein said reagent is a phosphorous compound capable of forming coordination bonds with said catalyst.

13. The process of claim 1 wherein at least one of $X^1$, $X^2$, and $X^3$ is individually said carboxylate, or said sulfonate, said carboxylate and said sulfonate individually containing, as cations, alkali metal, alkaline earth metal, zinc, ammonium, or quaternary ammonium ions of the formula $N(R^3R^4R^5R^6)$, wherein $R^3$, $R^4$, $R^5$ and $R^6$ individually represent a straight or branched chain alkyl group having 1 to 4 carbon atoms.

14. The process of claim 1 wherein each of $Ar^1$, $Ar^2$ and $Ar^3$ is phenyl.

15. The process of claim 1 wherein each of $X^1$, $X^2$, and $X^3$ is sulfonate.

16. The process of claim 1 wherein each of $m_1$, $m_2$, and $m_3$ is 0 or 1, the sum of $m_1$, $m_2$, and $m_3$ being 1, 2, or 3.

17. The process of claim 1 wherein each of $Ar^1$, $Ar^2$ and $Ar^3$ is phenyl, each of $X^1$, $X^2$, and $X^3$ is sulfonate, each of $m_1$, $m_2$, and $m_3$ is 0 or 1, the sum of $m_1$, $m_2$, and $m_3$ being 1, 2, or 3.

18. The process of claim 1 wherein there is at least 100 mols of carbon monoxide or the equivalent amount of said carbon monoxide forming compound present per gram-atom of rhodium in said distillation residue.

19. The process of claim 18 wherein there is 300 to 1000 mols of carbon monoxide or the equivalent amount of said carbon monoxide forming compound per gram-atom of rhodium in said distillation residue.

20. The process of claim 1 wherein the reaction with the aqueous solution of complex reagent takes place at a reaction temperature of 50° C. to 160° C.

21. The process of claim 1 wherein reaction with the aqueous solution of complex reagent takes place under a reaction pressure of 10 to 40 MPa.

22. The process of claim 1 wherein the reaction with the aqueous solution of complex reagent is carried out for a period of 0.1 to 10 hours.

23. The process of claim 22 wherein said carbon monoxide is contained in a mixture of gases.

24. The process of claim 23 wherein said gases are synthesis gas.

25. The process of claim 1 wherein said carbon monoxide forming compound is an aqueous formaldehyde solution.

26. The process of claim 1 wherein said organic phase is further washed with water.

27. The process of claim 1 wherein said distillation residue result from hydroformylation of ethylene and terminally and internally branched olefins.

28. The process of claim 17 wherein said reagent is triphenylphosphine-trisulfonate, triphenylphosphine-disulfonate, or mixtures thereof.

* * * * *